(12) United States Patent
Soldani et al.

(10) Patent No.: US 8,628,787 B2
(45) Date of Patent: Jan. 14, 2014

(54) METHOD FOR PRODUCING A DEVICE APPLICABLE TO BIOLOGICAL TISSUES, PARTICULARLY A PATCH FOR TREATING DAMAGED TISSUES, AND A DEVICE OBTAINED BY SAID METHOD

(75) Inventors: Giorgio Soldani, Massa (IT); Enrica Briganti, Ortonovo (IT)

(73) Assignees: Consiglio Nazionale Delle Richerche, Rome (IT); Regione Toscana, Florence (IT)

( * ) Notice: Subject to any disclaimer, the term of this patent is extended or adjusted under 35 U.S.C. 154(b) by 0 days.

(21) Appl. No.: 13/322,215

(22) PCT Filed: May 26, 2010

(86) PCT No.: PCT/IB2010/052343
§ 371 (c)(1),
(2), (4) Date: Nov. 23, 2011

(87) PCT Pub. No.: WO2010/136983
PCT Pub. Date: Dec. 2, 2010

(65) Prior Publication Data
US 2012/0070485 A1    Mar. 22, 2012

(30) Foreign Application Priority Data

May 26, 2009   (IT) ................. PI2009A0066

(51) Int. Cl.
*A61L 15/32* (2006.01)
*A61L 15/42* (2006.01)
(52) U.S. Cl.
USPC ............... 424/400; 424/426; 514/13; 514/20
(58) Field of Classification Search
None
See application file for complete search history.

(56) References Cited

U.S. PATENT DOCUMENTS

| 6,056,970 A * | 5/2000 | Greenawalt et al. .......... 424/426 |
| 6,762,336 B1 * | 7/2004 | MacPhee et al. ............... 602/48 |
| 2005/0118144 A1 * | 6/2005 | Zhang .......................... 424/93.7 |

OTHER PUBLICATIONS

Brignanti et al., Title: Silicone based polyurethane materials: a promising biocompatible elastomeric formulation for cardiocascular applications. J. Material Science: Mater Med (2006) 17:259-266; published 2006, bi Springer.*

* cited by examiner

*Primary Examiner* — Janet Epps-Smith
*Assistant Examiner* — Yanzhi Zhang
(74) *Attorney, Agent, or Firm* — Abelman, Frayne & Schwab (57) ABSTRACT

The present invention relates to a device consisting of cross-linked nanofibrillary fibrin supported on and rooted to a microporous nonwoven fabric consisting of a biocompatible synthetic polymer material. An active ingredient is advantageously dispersed in the fibrin layer. The fibrin layer does not have a haemostatic function, but is suitable for retaining the active ingredient and releasing it with controlled kinetics. The device forming the object of the invention, preferably in the form of patches, is useful for in vitro cell cultures or for treating tissues damaged by wounds or necrosis, such as cardiac walls bearing the sequelae of infarction, or a tissue damaged by a diabetic ulcer. The patch according to the invention can be manufactured by inducing the polymerisation of the fibrin, under suitable conditions, directly on the support layer, which is suitably impregnated with thrombin (at least in a superficial portion of its thickness), and which has been conveniently prepared by means of a spray phase-inversion technique.

12 Claims, 4 Drawing Sheets

METHOD FOR PRODUCING A DEVICE APPLICABLE TO BIOLOGICAL TISSUES, PARTICULARLY A PATCH FOR TREATING DAMAGED TISSUES, AND A DEVICE OBTAINED BY SAID METHOD

CROSS-REFERENCE TO RELATED APPLICATIONS

This application is a National Phase of PCT/IB2010/052343, filed 26 May, 2010 which claims priority from Italian Application No. PI2009A000066, filed 26 May 2009, both of which are incorporated herein by reference.

FIELD OF THE INVENTION

The present invention concerns a device for facilitating in vitro or in vivo cell growth, particularly for treating necrotic or damaged tissues also by means of its local administration of active ingredients, with controlled kinetics, and particularly of growth factors capable of inducing tissue revascularisation.

BRIEF OUTLINE OF THE KNOWN ART

The need is felt in the medical field to treat damaged tissues, such as tissue wounds due to diabetic ulcers, or cardiac walls with the sequelae of infarction, by inducing tissue regrowth.

The materials that are effective for this purpose are able to provide extracellular matrices suitable for the growth and migration of cell components, enabling the formation of biological tissues. Interest is focusing particularly on natural polymers that can be reabsorbed by the biological environment in which they are inserted, such as fibrin, a protein involved in biological processes such as blood coagulation, that undergoes a process of natural degradation called fibrinolysis, which enables it to be reabsorbed.

The functional recovery of such damaged tissues is also favoured by the administration of various active ingredients, e.g. antibiotics, anti-inflammatory agents or particular bioactive molecules, known as growth factors. The proangiogenic growth factors are particularly important because they are capable of contributing to the regeneration of soft tissues, inducing their revascularisation.

Some of the most well known among these factors are VEGF (vascular endothelial growth factors), bFGF (basic fibroblast growth factors) and proadrenomedullin N-terminal 20 peptide (PAMP), and they are suitable for treating the sequelae of cardiac ischaemia and chronic diabetic ulcers. Other growth factors can contribute to the repair of specific tissues. For instance, TGF-$\beta$1 (transforming growth factor-$\beta$1) and, here again, bFGF help to regenerate joint cartilage by promoting the proliferation of chondrocytes and the formation of extracellular matrix.

Growth factors can be administered locally in the form of a solution, but in this case they are easily separated from the tissue and/or rapidly degraded, giving rise to a drastic reduction in their therapeutic efficacy, which demands their administration with controllable kinetics.

A nanofibrillary matrix, such as that of fibrin, provides an ideal medium capable of stabilising (i.e. retaining and progressively releasing) growth factors, as well as other therapeutic agents, such as antibacterial and anti-inflammatory agents. Fibrin occurs naturally as a soft, gelatinous and amorphous mass, however, which means that it does not have the mechanical and structural characteristics, e.g. elastic modulus and tensile strength, needed to make it readily manageable and capable of withstanding the dynamic stresses of numerous physiological environments.

For the functional recovery of tissues damaged by various types of disorders, there is consequently a felt need for biocompatible media for keeping the tissues in contact with nanofibrillary matrices capable of supporting cellular processes that facilitate regeneration, advantageously in the form of patches for applying to said tissues. There is likewise a felt need for a patch capable of retaining therapeutic agents useful for said tissue regeneration process and releasing them gradually in the tissues being treated.

There are currently known structures, such as those described in U.S. Pat. No. 6,762,336 or in WO2008/019128, the use of which is limited to the haemostatic treatment of wounds.

Some of the structures described in said documents comprise alternating adjacent layers of thrombin and fibrinogen for placing in contact with the damaged tissue, with a layer of polymer serving as a means of support. Some embodiments of the structures described involve the interposing of a layer of a biocompatible binding material, or the addition of active ingredients to one of the layers. The above-mentioned bandages are prepared at low temperatures (0-4° C.) and the depositing of each layer is followed by a deep-freezing step (at −80° C.); in these conditions, the thrombin does not promote the formation of fibrin from the fibrinogen. The fibrin is consequently not contained in the bandages, it is formed only after the bandage has been applied to the wound, thus performing an exquisitely haemostatic function.

In addition to failing to ensure an adhesion sufficient to keep the structure together for the predictable application time, or to guarantee its stability in such a dynamic context as that of a cardiac wall, where intensive strain/deformation cycles take place, using this approach to combine the two layers considerably complicates the structure's manufacturing process and also restricts its utility to its haemostatic function.

US 2006/02204738 describes a composition for coating a medical device, said composition comprising a plurality of nanostructures (silicon, nickel or TiO2 nanofibers) dispersed in a matrix (fibrin also being listed among the many possible materials). Said composition is applied (in the form of a powder or paste) to medical devices of various types so as to constitute a nanostructured coating.

The object of the present invention is therefore a method for manufacturing a biocompatible structure that enables the stable application to a biological tissue of an extracellular matrix suitable for facilitating the growth and migration of cell components with therapeutic effects on said tissue.

Another object of the present invention is to produce such a structure, and particularly a device capable of releasing active ingredients into said tissue with predetermined kinetics.

A particular object of the present invention is to produce such a structure so that it enables the release of growth factors, and particularly of proangiogenic growth factors, into a damaged tissue with a controlled release rate in order to promote the recovery of said tissues, e.g. by means of a process of revascularisation or therapeutic angiogenesis.

Another object of the present invention is to produce a device, and a patch in particular, that has a structure suitable for use in tissue or organ reconstruction surgery, and particularly a structure suitable for cardiac reconstructive surgery, or suitable in any case for the repair of tissues liable to considerable strains. Another object of the present invention is a method for manufacturing said biocompatible structure that entails limited times and costs.

SUMMARY OF THE INVENTION

The above-listed objects, as well as others, are achieved by a patch structure for a biological tissue comprising:
- a support layer consisting of a biocompatible synthetic polymer material, said support player having a microporous nonwoven structure;
- a biological interaction layer consisting of a mesh of fibrin nanofibers, this biological interaction layer being rooted to the first layer and placed, when in use, in contact with the tissue, the main characteristic of the structure being that the rooting of the nanofibre mesh to the biocompatible polymer material is achieved by applying fibrinogen to the biocompatible polymer and previously dispersing thrombin in the biocompatible polymer.

In other words, the device forming the object of the present invention is cross-linked nanofibrillary fibrin supported by and rooted to a microporous nonwoven fabric made of a biocompatible synthetic polymer material. Thus, instead of a fibrin that is normally in the form of a soft, gelatinous and amorphous mass, the fibrin in this case is not haemostatic and its consistency, form and mechanical strength derive from the support to which it is rooted. The fibrin supported according to the invention takes a much longer time to undergo fibrinolysis than a fibrin lacking any support (i.e. several days rather than a few hours).

In the biological interaction layer there is advantageously dispersed an active ingredient, in particular a growth factor for treating tissue damage (caused by trauma, burns, diabetic ulcers, bedsores, etc), said biological interaction layer being designed to retain the active ingredient and release said active ingredient into the tissue.

Said device is useful for facilitating the in vitro or in vivo cell growth of biological tissues, for instance.

An object of the invention is also a method for producing the aforesaid patch structure designed to be applied to a biological tissue, the patch structure comprising:
- a support layer comprising a biocompatible polymer material;
- a biological interaction layer comprising a fibrin nanofiber mesh, the nanofibre mesh being prepared directly on the support layer starting from a precursor, fibrinogen;

said method involving the following steps:
- the preparation of a backing surface for the support layer;
- the preparation of a first solution containing the biocompatible polymer material and a second solution containing thrombin, an agent designed to facilitate the formation of the biological interaction layer starting from the precursor;
- the simultaneous distribution of the first solution and of the second solution on the backing surface, the simultaneous distribution so as to create in situ a mixture of the first solution with the second solution so that the support layer is formed by precipitation directly on the backing surface, and so that the support layer consists of the biocompatible polymer material and it is impregnated with thrombin;
- the application of the fibrinogen on the support layer, the fibrinogen being modified by the thrombin contained inside the support layer so as to form a layer of fibrin firmly bonded to the support layer;
- the application step in which the precursor is applied to the support layer, is carried out bringing the support layer into contact with a third solution containing the precursor and maintaining said contact for a given time and at a given temperature.

In other words, the biocompatible polymer material forms the support layer and contains—especially proximal to the exposed surface, on the side opposite the backing surface—a dispersion of thrombin, the agent that facilitates the formation of the mesh of fibrin nanofibres. When the fibrinogen, the precursor of the nanofibre mesh, comes into contact with said agent in suitable conditions of time and temperature, the nanofibre mesh begins to develop, firmly anchored (or rooted to, or interlaced, or interconnected with) the polymer material of the support layer. Dispersing the agent in the support layer creates the right conditions for consolidating the nanofibre mesh with said support and thereby obtaining, at the end of the process, a biological interaction layer firmly bonded to the support layer (in other words, the layer of fibrin forms directly inside the support layer and becomes rooted, at least superficially, within the thickness of the support).

The second solution consists of a liquid that is not a solvent for the biocompatible polymer material and the biocompatible polymer becomes deposited on the backing surface due to the effect of said non-solvent liquid during the in situ mixing of the first solution with the second solution. Said method preferably implemented by mixing the two solutions in situ on a backing surface provided by a spindle rotating and/or sliding along the axis of rotation—enables the rapid preparation of the support layer steeped with the agent designed to facilitate the formation of the nanofibre mesh. The resulting support layer has the structure of a microporous, mechanically resistant, nonwoven fabric material.

DETAILED DESCRIPTION OF THE INVENTION

Fibrin is a polymer of natural origin involved in numerous biological repair processes, and in blood coagulation in particular, and it is reabsorbed by means of a process known as fibrinolysis. Having formed from inside the support layer, the fibrin contained in the device according to the invention becomes organised in a cross-linked nanofibrillary structure that provides an extracellular matrix suitable for the growth and migration of cell components, enabling the formation of biological tissues. It consequently provides a substrate suitable for the regenerative treatment of damaged tissues and also for in vitro cell culture. It should be noted that, because the fibrin contained in the device according to the invention is already cross-linked, it does not have a haemostatic function when it is in contact with the damaged biological tissue; it serves instead as a three-dimensional extracellular matrix and vehicle for the controlled release of pharmacologically active ingredients.

The nanofibres preferably have a crosswise dimension in the range of 50 nanometers to 300 nanometers, and particularly in the range of 100 nanometers to 200 nanometers. In addition to providing an ideal extracellular matrix for facilitating cell processes useful for tissue regeneration, the nanofibrillary structure enables the incorporation of substances such as active ingredients, and growth factors in particular, restricting their mobility within the biological interaction layer so that their diffusion or migration and subsequent release into the tissue to regenerate takes place gradually, with slower kinetics that are consequently more readily controllable according to the dimension, and the diameter in particular, of the nanofibres.

The cross-linked nanofibrillary structure is achieved in specific processing conditions, i.e. by treating the fibrinogen with a specific enzyme (thrombin) in specific temperature conditions (approximately 37° C.) and for a preset time (at least 6 hours). This enables full control over the conditions leading to the formation of the fibrin starting from fibrinogen. The cross-linking between the fibrin macromolecules is made possible by a particular enzyme, called factor XIII, or the fibrin stabiliser factor.

Together with the fibrinogen, the third solution contains a quantity of factor XIII in a concentration in the range of 5 to 60 international units per milliliter, and preferably in the range of 5 to 30 international units per milliliter.

In particular, the fibrinogen can be used mixed with a fibrinolysis inhibitor so as to prolong the useful life of the patch, and particularly to prolong the time of administration of the active ingredients.

Together with the fibrinogen and the factor XIII, the third solution preferably contains a quantity of aprotinin in a concentration in the range of 1000 to 5000 KIU (kallidogenase inactivation units) per milliliter, and preferably between 2000 e 4000 KIU per milliliter.

The fibrinogen and thrombin are preferably of human origin, or they may be obtained from other mammals.

The thrombin is preferably contained in the second solution in concentrations in the range of 10 to 500 international units per milliliter, and in particular in the range of 15 to 50 international units per milliliter.

Together with the thrombin, the second solution contains a quantity of calcium chloride in a concentration in the range of 5 to 30 nM, and in particular between 10 and 20 nM.

The application step in which the precursor is applied to the support layer can advantageously be completed according to a method chosen from among the following:
- sprinkling the support layer with a solution containing the precursor;
- removing the consolidated support layer from the backing surface and immersing the support layer in the precursor, maintained at a preset temperature. In the case of fibrin in particular, the immersion method, preferably conducted at a temperature near 37° C., e.g. in the range of 32 to 42° C. or, better still, between 35 and 39° C., enables particularly uniform biological interaction layers to be obtained.

The fibrinogen is advantageously contained in the aqueous solution in a concentration in the range of 10 mg/ml to 50 mg/ml; in particular, it has a concentration in the range of 15 mg/ml to 25 mg/ml.

During the simultaneous distribution step, there is advantageously a step in which the concentration varies for one of the substances, chosen from among:
- the biocompatible polymer material in the first solution;
- the agent intended to facilitate the formation of the biological interaction layer starting from the precursor; or
- both the above substances.

In particular, the concentration of the agent intended to facilitate the formation of the nanofibre mesh increases from a minimum level (e.g. 0 IU/ml) to a maximum level (e.g. 10-50 IU/ml) during the step in which the first solution and the second solution are simultaneously distributed. The agent is thus concentrated in the areas more proximal to the surface of the support layer, where the interaction with the fibrinogen takes place. This enables the quantity of thrombin used to be contained. The same goal is also achieved by the choice of the synthetic material used in the preparation of the support layer, through which the agent shows a limited tendency for molecular diffusion. This is the case, for instance, of thrombin in relation to materials made from aromatic polyurethanes and silicones.

By means of the method according to the invention it is possible to produce a patch structure preferably for the administration of an active ingredient in a biological tissue, for instance for administering a growth factor in a damaged tissue so as to facilitate the latter's recovery; in this case, during the preparation of the biological interaction layer, the precursor is used in a mixture or in a solution together with the active ingredient, i.e. it contains the active ingredient.

In particular, the active ingredient is a proangiogenic growth factor designed to induce the revascularisation of the damaged tissue, such as a proangiogenic growth factor chosen from among:
- VEGF (vascular endothelial growth factors);
- bFGF (basic fibroblast growth factors);
- PAMP (proadrenomedullin N-terminal 20 peptide); or
- a combination of the above growth factors.

Alternatively, the growth factor may be a relaxin, or one or more active ingredients derived from a platelet lysate (PDGF), or a combination of relaxin and said active ingredients.

Alternatively, the growth factor may be an insulin-like growth factor, IGF-1 or IGF-2, or the epidermal growth factor (EGF), or a transforming growth factor TGF-β, osteogenin, HBGF-1, HBGF-2.

Moreover, the structure according to the invention can include a combination of growth factors chosen from among those listed above, as well as their biologically active derivatives, mixed with one another and/or with said growth factors.

In addition to a growth factor, the active ingredient may be nitric oxide or an agent with antimicrobial and/or antibiotic, and/or antiseptic, and/or antiviral, and/or analgesic, and/or anti-inflammatory properties, or vitamins.

According to a particular embodiment of the invention, the patch structure may comprise nanoparticles, and particularly polymer nanoparticles charged with an active ingredient, and designed to release said active ingredient into the tissue over a preset period of time. This enables the timing of the controlled administration of the active ingredient to be extended beyond the limit imposed by the degradation of the patch structure in the biological environment.

The nanoparticles can be dispersed within the thickness of the support layer and/or within the nanofibre mesh of the biological interaction layer. In the former case, they are added to the first solution containing the biocompatible polymer material; in the latter case, they are added to the third solution, which contains the precursor of the nanofibre mesh.

Said nanoparticles can be chosen from among:
- biodegradable polyesters, and particularly:
  - polylactic acid (PLA);
  - polyglycolic acid (PGA);
  - copolymers containing polylactic acid and polyglycolic acid (PLGA);
- linear or branched polycaprolactone (PCL) and/or its copolymers.

The biocompatible polymer material can include a synthetic polymer, such as a synthetic polymer chosen from among:
- polyglycolic acid (PGA), polylactic acid and their copolymers;
- polyhydroxybutyrate (PHB);
- polydioxanone;
- polyamino acids;
- polyethylene glycol (PEG);
- an aromatic or aliphatic polyurethane (PU), preferably a poly(ether)urethane(PEtU); an aromatic or aliphatic poly(ester)urethane (PEsU); or their copolymers and/or mixtures;

a silicone, preferably diacetoxy silyl terminated polydimethylsiloxane (PDMS);

a combination of the above polymers, and preferably a copolymer.

If the patch according to the invention is intended for tissues characterised by stiffness and strength, however, such as bone or ligaments, then the support layer material can be chosen, for instance, from: polyglycolic acid (PGA), polylactic acid and their copolymers; polyhydroxybutyrate (PHB), polydioxanone; polyamino acids, block copolymers of polyethylene glycol/polylactic acid (PELA); block copolymers of poly (D,L-lactic-co-glycolic) acid (PLGA)-polyethylene glycol (PEG)-poly (D,L-lactic-co-glycolic) acid (PLGA) [PLGA-PEG-PLGA]; block copolymers of polylactic acid (PLA)-polyethylene glycol (PEG)-polylactic acid (PLA) [PLA-PEG-PLA].

If the patch according to the invention is intended for tissues characterised instead by elasticity (such as the cardiovascular system or epidermis, for instance), then as a material for the support layer, the choice can be made among the polymers belonging to the class of elastomers, such as: aromatic or aliphatic poly(ether)urethane (PEtU), aromatic or aliphatic poly(ester)urethane (PEsU), or their copolymers and/or mixtures; silicones and their copolymers and/or mixtures; linear or branched polycaprolactone (PCL) and/or its copolymers and/or mixtures. In this last case, the elastomeric component gives the structure according to the invention the features of mechanical strength and elasticity needed for applications on tissues that have certain elastic characteristics. In fact, this choice of material for the support layer gives rise to structures with a modulus of elasticity resembling that of a large proportion of biological tissues; in particular, the modulus of elasticity comes in the range of 0.3 MPa to 1.5 MPa, which are values similar to those characteristic of the human myocardium.

As for the biodegradability of the support, this may be modulated by using combinations of the above-listed materials, according to methods known to a person skilled in the art, depending on the needs of the tissue to treat and the active ingredients to release.

In fact, many polyurethanes have a distinctively high biodegradability: this property can be mitigated by means of their copolymerisation with silicones, obtaining copolymers that are still degradable in vivo, but with slower kinetics, in order to prolong the time the patch remains in the tissue.

In particular, such a combination of polyurethane and silicone comprises from 15 to 40 parts by weight of silicone, and in particular from 25 to 35 parts by weight of silicone.

BRIEF DESCRIPTION OF THE DRAWINGS

Further characteristics of the present invention emerge more clearly from the following description of its embodiments, given here as an example, with reference to the attached drawings, wherein.

DESCRIPTION OF PREFERRED EMBODIMENTS

Figure 1:
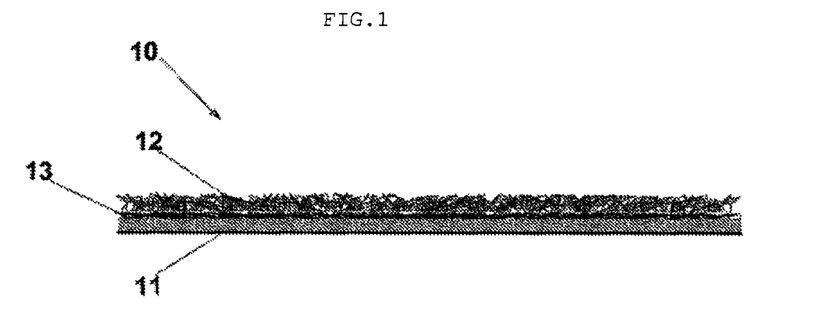
FIG. 1 schematically shows the layers of the device according to the invention.

Referring to FIG. 1, a device according to the invention is described that consists of a patch 10, within the structure of which the following are recognizable:

a support layer 11 made of a synthetic polymer, in particular with a combination of polyether urethane (PEtU) and diacetoxy silyl terminated (tetraacetoxy functional) polydimethylsiloxane (PDMS);

a biological interaction layer 12, consisting of a three-dimensional nanofibrillary fibrin mesh, i.e. consisting of fibres with a diameter of less than 1μ, and in particular of fibres around 100 nanometers in diameter. Said mesh is suitable for retaining and gradually releasing growth factors and other therapeutic agents.

The layer 11 of the patch 10 provides support for the nanofibrillary matrix of the layer 12 and can be obtained by means of spray phase-inversion technique, that is by precipitation of the synthetic polymer from a solution thereof in an organic solvent by mixing with a liquid that is not a solvent for the polymer (typically water). Said method can be carried out using, for instance, the spray machine 20 schematically illustrated in FIG. 2 and described in PCT WO2004/054775. It comprises a spindle 21 that provides a backing surface for the support layer; the spindle 21 can rotate around an axis 22 and slide in the direction indicated by the arrow 37. The spray machine 20 also comprises two spray guns 23 and 24, hydraulically connected by means of corresponding pipes 25 and 26 to two pumps 27 and 28 that respectively deliver a first and a second solution. By means of respective further pipes 29 and 30, the spray guns 23 and 24 can receive compressed air from a compressor 31 so as to create respective flows 32 and 33 of nebulised liquid towards the spindle 21. The spray gun 23 is supplied with solutions containing a biocompatible polymer, said supply being drawn sequentially from the tanks 34, each of which contains a solution with a different concentration of biocompatible polymer, and in this specific case of a PEtU-PMDS system in an organic solvent, e.g. a 1:1 volume/volume mixture of tetrahydrofuran and 1,4-dioxane. The concentration of the biocompatible polymer is advantageously varied during the course of the process, according to the details given below. The biocompatible polymer is obtainable from the reaction of medical-grade aromatic PEtU (e.g. Estane® 5714, Lubrizol Advanced Materials, Inc., Cleveland, Ohio, USA) and diacetoxy silyl terminated (tetraacetoxy functional) PDMS (e.g. United Chemical Technologies, Inc, Bristol, Pa., USA); the proportion of PMDS is preferably approximately 30% weight/volume of the total polymer.

Figure 2:
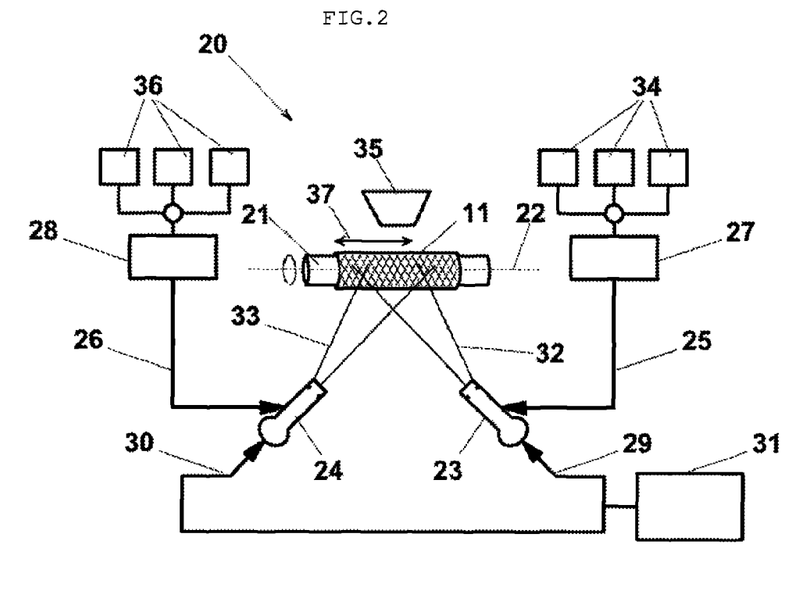
FIG. 2 schematically shows a "spray-machine" for use in a step in the process for manufacturing the device according to the invention.

The spray gun 24 is supplied with distilled water and subsequently with aqueous solutions containing thrombin and calcium chloride, said supply being drawn sequentially from the tanks 36, each of which contains a solution with a different concentration of thrombin.

The formation of the support layer 11 of the patch 10 is completed by placing the spindle 21 in rotation around the axis 20 and imposing thereon a reciprocating translatory motion in the direction 37, and simultaneously operating the spray guns 23 and 24 to deliver the above-mentioned liquids, according to the steps listed in table 1.

The duration of the spraying steps for the single solutions is expressed in terms of the number of forward and back cycles of the spindle 21. The presence in the flow 33 of a substance that is not a solvent for the polymer contained in the flow 32 induces the precipitation of the polymer on the rotating surface of the spindle 21, on which the support layer 11 forms. To facilitate said precipitation, or phase inversion, towards the end of the application (in step III in the example herein) the solution 32 may contain water, as shown in FIG. 2; an extractor unit 35 removes the excess solvents during the spraying process.

TABLE 1

| Step | Duration, number of cycles | Spray gun 23 | Spray gun 24 | Flow rate ml/min |
|---|---|---|---|---|
| I | 800 | 2.5% PU-PDMS | distilled water | 1.5 |
| II | 250 | 1% PU-PDMS | distilled water | 1.5 |
| III | 400 | 1% PU-PDMS dist. water + 17% water | thrombin aqueous solution | 1.5 |
| IV | 200 | — | thrombin aqueous solution | 1 |

Table 1 also shows the global flow rates of the two flows 32 and 33 adopted in an experimental machine.

Figure 3:
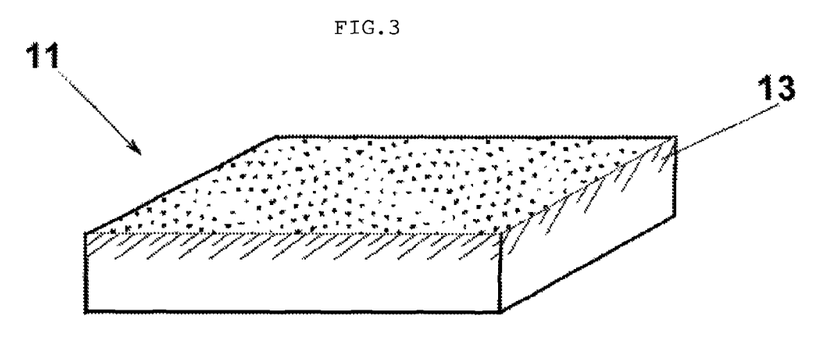
FIG. 3 schematically shows the support layer 11 of the structure according to the invention, wherein the superficial portion of its thickness is impregnated with thrombin.
Figure 4:
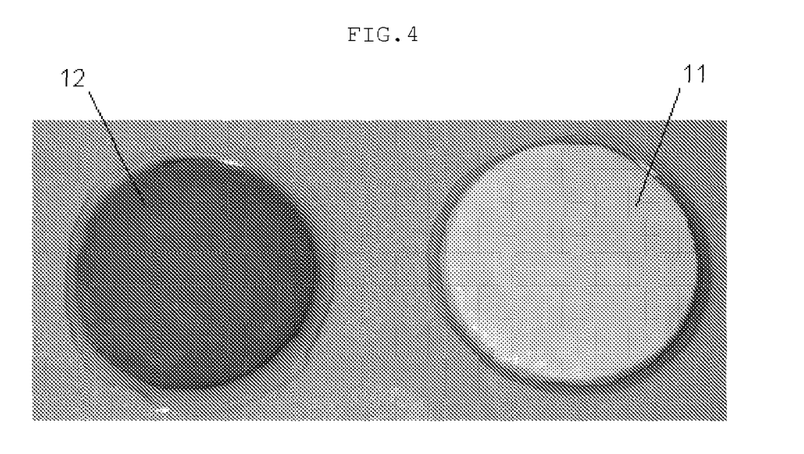
FIG. 4 shows for comparison an image of the patch 10 (showing the exposed surface of the biological interaction layer 12 consisting of fibrin; said exposed surface has an intense, uniform staining due to treatment with red Ponceau stain, for which fibrin has a particular affinity) and an image of the support layer 11, which contains no fibrin (used as a reference: it appears white because it is incapable of retaining the stain)
Figure 5:
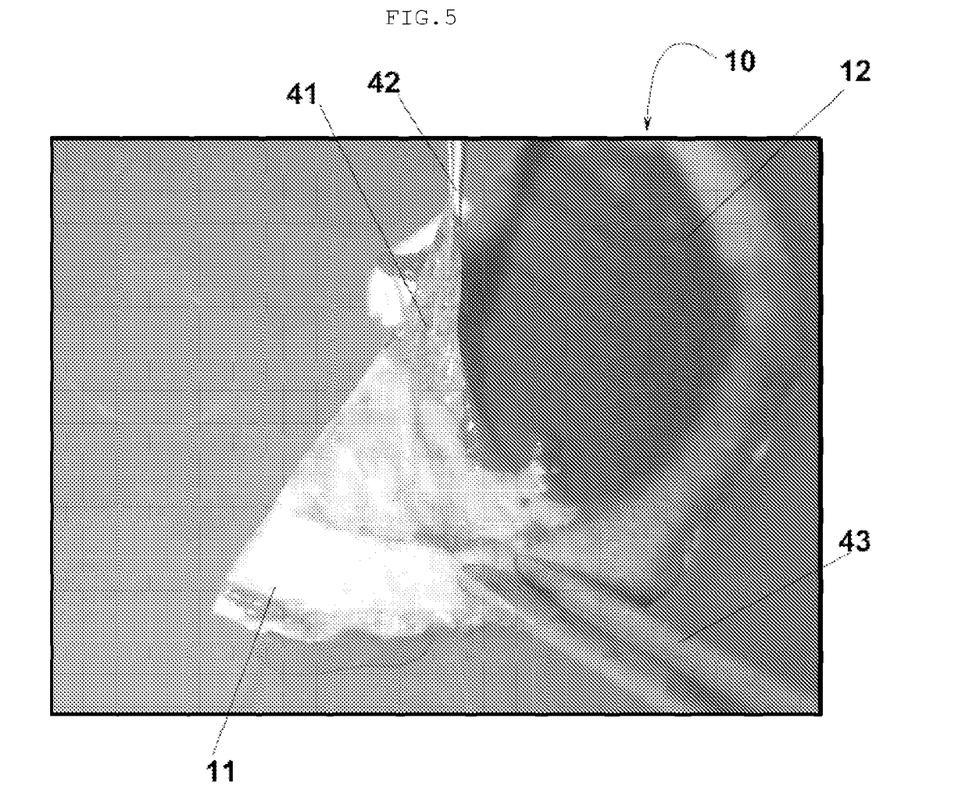
FIG. 5 shows a quality test of the detachment of the fibrin from the support layer according to the invention.
Figure 6:
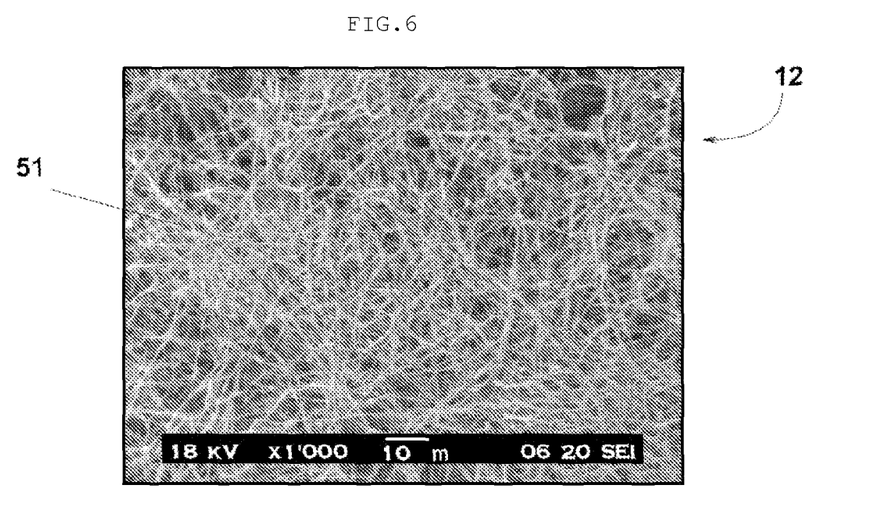
FIGS. 6 and 7 are two SEM images of the surface of the fibrin layer forming on a support layer according to the invention, with two different levels of magnification.
Figure 7:
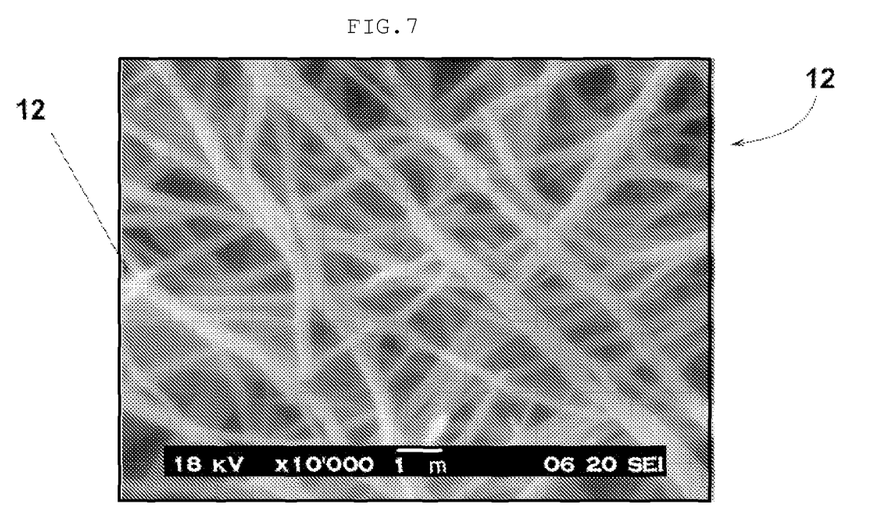

As shown schematically in FIG. 3, the presence of the thrombin in steps III and IV means that the support layer 11 has an area 13, proximal to the exposed surface, that is impregnated with thrombin, which is consequently available for interacting with the fibrinogen contained in the aqueous solution with which the layer 11 is placed in contact, preferably after its removal from the surface of the spindle 21, possibly reducing it to obtain conveniently-sized pieces. The concentration of fibrinogen is preferably in the range of 10 mg/ml to 30 mg/ml, and in particular it is near 20 mg/ml. Said concentration assures the advantages described below over a patch obtained from 10 mg/ml solutions of fibrinogen.

The aqueous solution can also contain active ingredients to incorporate in the fibrillary matrix of the biological interaction layer 12. In particular, to treat damaged tissues that require revascularisation, such as tissues affected by ulcers and cardiac walls with the sequelae of ischaemia, the layer 12 can be impregnated with active ingredients such as VEGF and bFGF, typically in a concentration of 200 ng/ml, and possibly also PAMP (proadrenomedullin) and/or relaxin. The fibrinogen becomes polymerised and forms fibrin, under normal conditions, completing the reaction after an incubation of several hours at 37° C. A step for stabilising the structure 10 thus obtained can be implemented by immersion in a physiological solution, while awaiting the structure's therapeutic usage.

Table 2 summarises several examples of suitable concentrations of the components of the aqueous solution used to form the layer of fibrin 12 bonded to the support layer 11. In particular, two groups, (a) and (b), of examples of patches according to the invention are distinguishable, obtained using concentrations of fibrinogen corresponding to 10 mg/ml and 20 mg/ml, while all the other conditions remain the same.

The thrombin contained in the superficial area 13 of the support layer 11 enables a stable adhesion of the fibrin formed in situ due to the interaction of the fibrinogen with the thrombin with which the surface area 13 of the support layer 11 is impregnated. This has been confirmed by morphological analyses on samples of products obtained according to the above-described procedure, using the spray machine 20 (see FIG. 4).

TABLE 2

| Group | Fibrinogen mg/ml | Thrombin IU/ml | Heparin μg/ml | VEGF ng/ml | bFGF ng/ml |
|---|---|---|---|---|---|
| a) | 10 | 25 | 5 | 200 | 200 |
| b) | 20 | 25 | 5 | 200 | 200 |

Referring to FIG. 5, the integration of the layer of fibrin 12 on the surface of the support layer 11 has also been confirmed by a manual peeling test: under the fibrin layer 12, lifted with the aid of tweezers 42, there is evidence of the presence of synthetic material 41, which demonstrates that the cohesion between the fibrin and the synthetic polymer is at least as good as the internal cohesion of the layer 11 of PEtU/PMDS in the operative conditions adopted to produce the patch 10.

FIGS. 6 and 7 are images of the nanofibrillary surface of the biological interaction layer 12 on the patch 10, obtained by means of a scanning electron microscope (SEM, Jeol 5600, Jeol Italia) after metalizing with gold-palladium by means of a sputtering device (Sputter coater S150B, Edwards). The SEM micrographs correspond to magnifications of 1,000 and 10,000. Using a computer-based analytical process, these images enable the mean diameter of the fibres 51 of the fibrin mesh to be determined. There is evidence of the three-dimensional cross-linked fibrin structure of the biological interaction layer 12, consisting of randomly-oriented nanofibres 51. In particular, the nanofibres 51 obtained in the conditions used for group (a) in table 2 have a mean diameter of 165 nanometers, while those obtained in the conditions used for group (b), with twice the concentration of fibrinogen in the aqueous solution, have a narrower mean diameter, i.e. 131 nanometers.

As shown in the diagram in FIG. 8, the structure according to the invention, in the embodiment (b), obtained using a concentration of 20 mg/ml of fibrinogen, completes the release of the growth factors bFGF and VEGF in approximately 1 week. This is a considerably longer administration time than is achievable with natural fibrin, in which case the release of the bFGF is completed in approximately 3 days. This is probably attributable to a greater degree of cross-linking of the fibrin achieved using the method according to the invention, which suffices to delay the diffusion of the growth factors from the inside to the outside of the matrix.

The rate of release V of both types of growth factor also depends on the concentration of fibrinogen F; in particular, it diminishes when the concentration goes from 10 mg/ml to 20 mg/ml. In the former case, almost all of the VEGF and bFGF is released within four days, while in the latter case the percentages of the two factors released during the same time interval drops to around 80% and 70%. Observation under the scanning electron microscope shows that the diameter of the nanofibres 51 diminishes considerably when the concentration of fibrinogen increases from 10 mg/ml to 20 mg/ml. This can be explained by an increase in the fibrin peptide splitting rates, facilitated by the higher concentration of fibrinogen, which accelerates the production of fibrin monomers.

Figure 8:
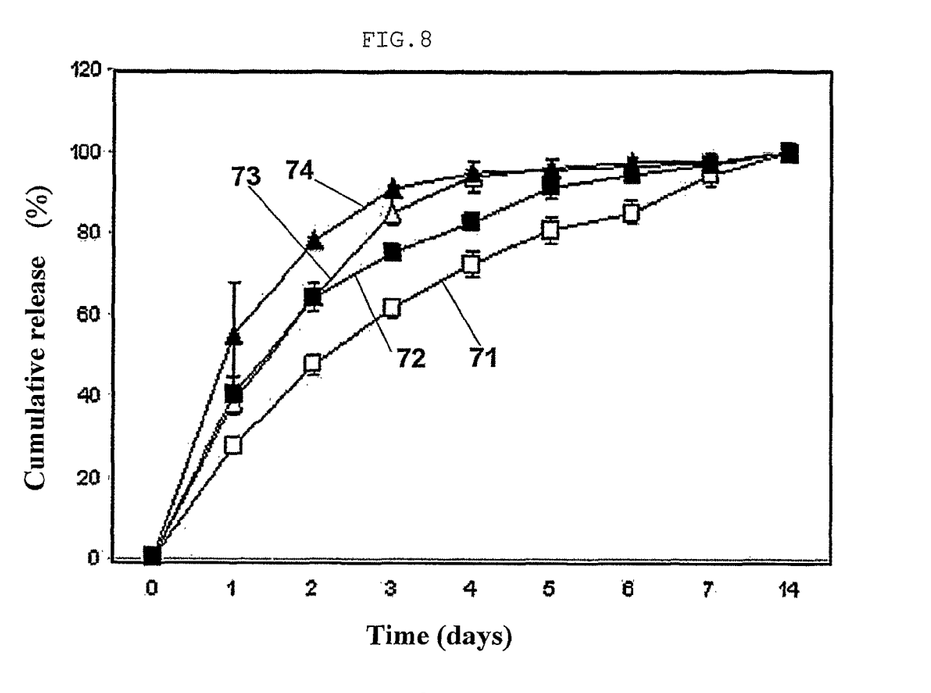
FIG. 8 shows diagrams of the release of growth factors VEGF and bFGF from two patch structures according to the invention, obtained using two different concentrations of fibrinogen.

As is deducible if the curves 71,73 are compared with the curves 72,74, moreover, bFGF is released with slower kinetics than VEGF. This confirms findings in previous studies conducted on fibrin: the lower rate of release of bFGF can be explained by a more stable bonding of the bFGF to the fibrin mesh than in the case of VEGF. The two growth factors have different, complementary roles in the induction of angiogenesis: VEGF takes effect as an initiator of the blood vessel formation process, while bFGF contributes to the vessels' subsequent development, and therefore demands longer application times. A differentiated rate of release, as shown in FIG. 8, is consequently a condition that favours the synergic effect of the two growth factors.

The rate of release of the growth factors can be determined by repeating the enzyme-linked immunosorbent assay, or ELISA test (Quantikine®, &D Systems Europe, Abingdon, UK) at regular intervals in a specifically prepared culture medium.

The biological activity of the growth factors released by the patch according to the invention is indicated by data on the in vitro proliferation of HUVEC (human umbilical vein endothelial cells), comparing the results obtained on placing bFGF in a culture medium by means of a patch according to the invention with the results obtained on adding the growth factors in their free state. Observations have shown a biological activity that remains unchanged over time.

Mechanical tests conducted according to the ASTM D412-98a on rectangular samples with the structure of the patch 10 enabled its mechanical properties to be expressed as shown in table 3. These results refer to a constant increment of the load up to failure, and to test samples kept wet throughout the test in order to simulate their conditions of use.

First of all, there were no substantial differences when the mechanical properties were measured applying the stress in different directions, i.e. the materials have a substantially isotropic behaviour.

TABLE 3

|     | E (MPa) | $\sigma_Y$ (MPa) | $\epsilon_Y$ (%) | $\sigma_{max}$ (MPa) | $\epsilon_{max}$ (%) |
| --- | --- | --- | --- | --- | --- |
| 0°  | 0.6177 ± 0.07 | 0.3544 ± 0.012 | 145.533 ± 24.1 | 0.5547 ± 0.14 | 299.3 ± 51.59 |
| 45° | 0.653 ± 0.04 | 0.365 ± 0.077 | 145.33 ± 26.3 | 0.46 ± 0.19 | 231.866 ± 55.7 |
| 90° | 0.5947 ± 0.1 | 0.3743 ± 0.05 | 159.067 ± 18.67 | 0.6623 ± 0.09 | 338.4 ± 31.4 |

Moreover, the structure was distinctive in its capacity to withstand high strains without deteriorating. The elastic modulus E was nearly 0.6 MPa, and the yield strength $\sigma_Y$ and corresponding elongation were respectively around 0.36 MPa and 150%. The measurements were obtained using the instrumentation summarised in table 4.

TABLE 4

| Quantity | Type of instrument | Instrument model |
| --- | --- | --- |
| Thickness | Micrometer | range 293-IP65, $\epsilon$ ± 0.001 mm, RS Components S.p.A. |
| Length and width | Precision gauge $\epsilon$ ± 0.03 mm | RS components S.p.A. |
| Tensile properties (1) | Tensile testing machine | H10 kT, Tinius Olsen, R&D Srl, with 100 N loading cells. |

(1) Young's elastic modulus E, yield strength σY, percentage elongation at yield point εY, ultimate strength σmax, percentage elongation at failure εmax.

Tests on the immune response induced by the patch according to the invention identified no significant expression of gene markers of inflammatory response in monocytes submitted to variable incubation times, by comparison with findings in reference materials such as low-density polyethylene (LDPE).

Figure 9:
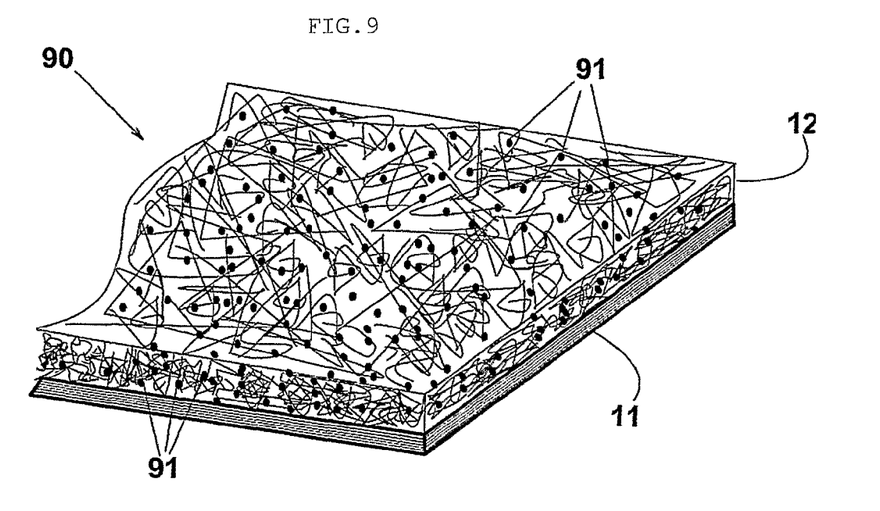
FIG. 9 is a schematic representation of a device according to the invention, in which nanoparticles are inserted.

Referring to FIG. 9, the patch 90 according to the invention can contain nanoparticles 91, and particularly nanospheres, made for instance with biodegradable polyesters such as polylactic acid (PLA), polyglycolic acid (PGA) and their copolymers; linear or branched polycaprolactone (PCL) and its copolymers. These nanoparticles can be associated with the active ingredients, and in particular they can be charged with the above-mentioned growth factors so as to prolong the controlled administration of said ingredients beyond the limits dictated by the degradation of the patch structure in the biological environment in which it is placed.

The above description of a specific embodiment suffices to illustrate the invention from the conceptual standpoint so that others, using the known art, can modify and/or adapt said specific embodiment to various applications without further research and without departing from the scope of the invention, on the understanding that any such adaptations and modifications shall be considered as equivalent to the embodiment described herein. The means and materials used to implement the various functions described may vary in nature without departing from the scope of the invention. Clearly, the expressions or terminology used herein are non-limiting and used merely for descriptive purposes. In other words, the invention as described above concerns:

1. A device, preferably having a planar form, such as a patch, and comprising:
   a support layer consisting of a biocompatible synthetic polymer material with a microporous nonwoven structure;
   a layer of fibrin with a cross-linked nanofibrillary structure; wherein said fibrin layer is rooted in (i.e. its fibres are inserted within) the support layer.
2. A device as in item 1, wherein at least one active ingredient is dispersed in the fibrin layer.
3. A device as in item 2, wherein said active ingredient is chosen from among:
   a substance with antimicrobial and/or antibiotic, and/or antiseptic and/or antiviral, and/or analgesic, and/or anti-inflammatory properties, and vitamins;
   nitric oxide;
   a proangiogenic growth factor suitable for inducing the revascularisation of a damaged tissue;
   VEGF (vascular endothelial growth factors);
   bFGF (basic fibroblast growth factors);
   PAMP (proadrenomedullin);
   a relaxin;
   a growth factor derived from a platelet lysate;
   an insulin-like growth factor, particularly IGF1 and/or IGF2;
   EGF, epidermal growth factor;
   a transforming growth factor, TGF-β;
   osteogenin;
   a bone tissue growth factor;
   a collagen growth factor;

a cytokine;
an interferon;
a hormone;
a heparin binding growth factor HBGF-1 and/or HBGF-2;
a biologically active derivative of one or more of the above-listed growth factors;
any combination of said growth factors and/or said derivatives.

4. A device according to any of the items 1-3, wherein the support layer of said device consists of a biocompatible polymer chosen from among:
polyurethanes or their copolymers and/or mixtures; silicones and their copolymers and/or mixtures;
linear or branched polycaprolactone (PCL) and/or its copolymers and/or mixtures; polyglycolic acid (PGA), polylactic acid and their copolymers;
polyhydroxybutyrate (PHB);
polydioxanone;
polyamino acids;
block copolymers of polyethylene glycol/polylactic acid (PELA);
block copolymers of poly (D,L-lactic-co-glycolic) acid (PLGA)-polyethylene glycol (PEG)-poly (D,L-lactic-co-glycolic) acid (PLGA) [PLGA-PEG-PLGA];
block copolymers of polylactic acid (PLA)-polyethylene glycol (PEG)-polylactic acid (PLA) [PLA-PEG-PLA];
a combination of the above-listed polymers.

5. A device as in item 4, wherein said polyurethane (PU) is an aromatic or aliphatic poly(ether)urethane(PEtU), or an aromatic or aliphatic poly(ester)urethane(PEsU), or their copolymers and/or mixtures, and said silicone is a diacetoxy silyl terminated polydimethylsiloxane (PDMS).

6. A device as in item 5, wherein said elastomeric material is a copolymer comprising from 15 to 40 parts by weight of silicone.

7. A device as in any of the items 1-6 for medical use.

8. A device as in item 7, used in the treatment of damaged and/or necrotic biological tissues.

9. A device as in item 7 for use in reconstructive cardiac surgery or in the treatment of diabetic ulcers, or in the treatment of burns.

10 A device as in item 7 for use in tissue engineering.

11 A process for manufacturing a device according to any of the items 1-6, said process comprising the following steps:
(i) the preparation of the support layer by means of spray phase-inversion technique, wherein a solution containing thrombin is sprayed during at least one spraying step;
(ii) the treatment of the support layer obtained from step (i) with a solution containing fibrinogen and factor XIII, and possibly also one or more active ingredients;
(iii) incubation in conditions suitable for the formation of cross-linked nanofibrillary fibrin.

12 A process according to item 9, wherein the incubation is conducted at 32-42° C. for at least six hours.

13 A process according to items 9-10, wherein step (ii) is completed by immersing the support layer in a solution containing fibrinogen at a concentration in the range of 10 to 50 mg/ml, factor XIII at a concentration in the range of 5 to 60 international units per milliliter, and possibly one or more active ingredients.

14. Use of the device according to any of the items 1-6 for in vitro cell cultures.

The invention claimed is:

1. A patch structure for a biological tissue consisting of:
a support layer consisting of a biocompatible polymer material having a nonwoven microporous structure, said polymer further having thrombin dispersed within and treated with fibrinogen;
a biological interaction layer consisting of an active ingredient and a fibrin nanofiber mesh;
a biological interaction layer consisting of an active ingredient and a fibrin nanofiber mesh;
wherein said treatment results in the formation of fibrin and the anchoring of the support layer to the interaction layer.

2. The patch structure according to claim 1, wherein the active ingredient is selected from the group consisting of:
an antimicrobial agent, an antibiotic agent, an antiseptic agent, an antiviral, an analgesic agent, an anti-inflammatory;
a vitamin;
nitric oxide;
a growth factor selected from the group consisting of a proangiogenic growth factor suitable for inducing revascularisation in said damaged tissue;
VEGF (vascular endothelial growth factors);
bFGF (basic fibroblast growth factors);
PAMP (proadrenomedullin);
a relaxin;
a platelet derived growth factor (PDGF);
an insulin growth factor selected from the group consists of IGF1 and IGF1, paticularly IGF1 and/or IGF2;
EGF, epidermal growth factor;
a transforming growth factor, TGF-β;
osteogenin;
a bone tissue growth factor;
a collagen growth factor;
a cytokine;
an interferon;
a hormone;
heparin binding growth factors and combinations thereof.

3. The patch structure according to claim 1, wherein said biocompatible polymer material comprises a synthetic polymer selected from the group consisting of:
polyurethanes or their copolymers and/or mixtures;
silicones and their copolymers and/or mixtures;
linear or branched polycaprolactone (PCL) and/or its copolymers and/or mixtures; polyglycolic acid (PGA), polylactic acid and their copolymers;
polyhydroxybutyrate (PHB);
polydioxanone;
polyamino acids;
block copolymers of polyethylene glycol/polylactic acid (PELA);
block copolymers of poly (D,L-lactic-co-glycolic) acid (PLGA) - polyethylene glycol (PEG) - poly (D,L-lactic-co-glycolic) acid (PLGA) [PLGA-PEG-PLGA];
block copolymers of polylactic acid (PLA) - polyethylene glycol (PEG) -polylactic acid (PLA) [PLA-PEG-PLA]; and
a combination of the above-listed polymers.

4. The patch structure according to claim 3, wherein said biocompatible polymer material comprises a synthetic polymer, particularly a synthetic polymer selected from the group consisting of:
a polyurethane (PU);
a silicone; and
a combination of said polymers, particularly a copolymer, said combination comprising from 15 to 40 parts by weight of silicones, and in particular from 25 to 35 parts by weight of silicone.

5. The patch structure according to claim 2, wherein a portion of said active ingredient is associated with polymer nanoparticles charged with said active ingredient and designed to release it into said tissue over a pre-set period of time, said polymer nanoparticles being selected from the group consisting of:
  biodegradable polyesters, and in particular:
  polylactic acid (PLA);
  polyglycolic acid (PGA);
  copolymers containing polylactic acid and polyglycolic acid (PLGA); and
  linear or branched polycaprolactone (PCL) and its copolymers.

6. The method for manufacturing a patch structure according to claims 1,
  said method involving the following steps:
  the preparation of a backing surface for said support layer;
  the preparation of a first solution containing said biocompatible polymer material and of a second solution containing thrombin, an agent suitable for facilitating the formation of said biological interaction layer starting from a fibrin precursor;
  the simultaneous distribution of said first solution and said second solution on said backing surface, said distribution forming a mixture of said first solution with said second solution such that said support layer is formed by precipitation directly onto said backing surface, and such that said support layer includes said biocompatible polymer material and said agent, incorporated in said biocompatible polymer material;
  the application of said precursor on said support layer, said precursor being modified by said agent contained in said support layer so as to form said biological interaction layer firmly bonded to said support layer;
  wherein said application step is completed by bringing said support layer into contact with said precursor and maintaining said contact for a preset time and at a preset temperature.

7. The method according to claim 6, wherein:
  said fibrin precursor is an aqueous solution containing fibrinogen and factor XIII; said fibrinogen has a concentration in said aqueous solution in the range of 10 mg/ml to 50 mg/ml; and said factor XIII has a concentration in said solution in the range of 5 to 60 IU/ml;
  said agent for facilitating the formation of said nanofibre mesh is thrombin; said thrombin has a concentration in said second solution in the range of 10 to 500 international units per milliliter.

8. The method according to claim 6, wherein said application step is completed according to a method selected from the group consisting of the following:
  sprinkling said support layer with a solution containing said precursor;
  removing said consolidated support layer from said backing surface and immersing said support layer in said precursor, maintained at a preset temperature.

9. The method according to claim 6, wherein, during said simultaneous distribution step, there is also a step in which there is a variation in the concentration of one of the substances selected from the group consisting of:
  said biocompatible polymer material in said first solution;
  said agent for facilitating the formation of said biological interaction layer starting from said precursor;
  both of the previous substances;
  in particular said concentration of said agent is increased from a minimum level to a maximum level during said step for the simultaneous distribution of said first solution and said second solution.

10. The method according to claim 6, wherein said precursor contains an active ingredient in a preset concentration, such that said patch structure is suitable for releasing the active ingredient into said tissue, designed to facilitate the recovery of said damaged tissue.

11. The patch according to claim 4, wherein the polyurethane is (polyether) urethane (PEtU) and the silicone is diacetoxy silyl terminated polydimethyl siloxane (PDMS).

12. The method according to claim 10, wherein said active ingredient is a growth factor.

* * * * *